(12) United States Patent
Howard, III

(10) Patent No.: US 7,254,503 B2
(45) Date of Patent: Aug. 7, 2007

(54) LIGHT SOURCE WAVELENGTH CORRECTION

(75) Inventor: Willis E. Howard, III, Elkhart, IN (US)

(73) Assignee: Siemens Medical Solutions Diagnostics, Tarrytown, NY (US)

( * ) Notice: Subject to any disclaimer, the term of this patent is extended or adjusted under 35 U.S.C. 154(b) by 0 days.

(21) Appl. No.: 10/560,440

(22) PCT Filed: Jun. 3, 2004

(86) PCT No.: PCT/US2004/017340

§ 371 (c)(1),
(2), (4) Date: Dec. 12, 2005

(87) PCT Pub. No.: WO2004/109261

PCT Pub. Date: Dec. 16, 2004

(65) Prior Publication Data

US 2006/0139649 A1 Jun. 29, 2006

Related U.S. Application Data

(60) Provisional application No. 60/475,288, filed on Jun. 3, 2003.

(51) Int. Cl.
*G01N 21/55* (2006.01)
(52) U.S. Cl. .................. 702/85; 702/93; 702/28; 205/221; 205/205; 205/226; 356/73.1; 356/445; 356/320

(58) Field of Classification Search .................. 702/85, 702/93, 28; 356/319–320, 328, 445, 73.1, 356/39; 250/227.23, 226, 221, 205
See application file for complete search history.

(56) References Cited

U.S. PATENT DOCUMENTS

| | | | | |
|---|---|---|---|---|
| 4,566,798 A | * | 1/1986 | Haas | .......................... 356/448 |
| 5,305,233 A | * | 4/1994 | Kawagoe et al. | ........... 356/320 |
| 5,359,192 A | * | 10/1994 | Williams et al. | ....... 250/227.23 |
| 5,879,294 A | * | 3/1999 | Anderson et al. | ........... 600/310 |
| 6,201,607 B1 | | 3/2001 | Roth et al. | |

FOREIGN PATENT DOCUMENTS

| | | |
|---|---|---|
| EP | 0 653 622 A1 | 5/1995 |
| EP | 0 816 829 A2 | 1/1998 |
| WO | WO 01/73405 A1 | 10/2001 |
| WO | WO 02/14793 | 2/2002 |

\* cited by examiner

*Primary Examiner*—John Barlow
*Assistant Examiner*—Hien Vo
(74) *Attorney, Agent, or Firm*—Toby H. Kusmer, P.C.; Noam Pollack

(57) ABSTRACT

A wavelength correction function provides corrected reflectance values from actual reflectance values taken in a reflectance-base instrument. The correction is provided as a function of measured reflectance values and a predefined set of high resolution reflectance values established for the reflectance-based instrument implementing the wavelength correction function.

27 Claims, 8 Drawing Sheets

LIGHT SOURCE WAVELENGTH CORRECTION

CROSS REFERENCES TO RELATED APPLICATIONS

This application claims the benefit of priority under 35 U.S.C. §119(e) from now abandoned, commonly owned U.S. provisional patent application Ser. No. 60/475,288, entitled DIAGNOSTIC INSTRUMENT, filed Jun. 3, 2003.

This application claims the benefit of priority under 35 U.S.C. §120 from co-pending, commonly owned U.S. non-provisional patent application Ser. No. 10/821,441, entitled TRAY ASSEMBLY FOR OPTICAL INSPECTION APPARATUS, filed Apr. 9, 2004.

FIELD OF THE INVENTION

The inventive concepts relate to reflectance-based systems and methods. More particularly, the present invention relates to systems and methods for wavelength correction within such systems and methods.

BACKGROUND

Reflectance-based instruments have long been in use in a variety of applications. One type of reflectance-based system is referred to as a "reflectometer", used to perform tests in certain medical and laboratory applications. In a typical form, a reflectometer includes one or more light sources configured to generate one or more light signals at given wavelengths. An object under test receives the signal and reflects a portion thereof—referred to as "reflectance". Reflectance is typically considered to be unit-less because it is defined as the ratio of the light actually leaving a sample to the amount that would leave if none were absorbed. In recent years, the National Institute of Standards and Technology (NIST) has defined reflectance in terms of this kind of mathematical model, rather than provide a physical reflectance standard. The perfect diffuse surface scatters light according to Lambert's law, which states that the intensity of light scattered from a point on a reflecting surface follows a cosine relationship with the polar angle of the scattered light, independent of the direction of the incident light. One or more detectors or sensors are oriented to receive the reflected signals. A processor analyzes the characteristics of the received reflected signals and produces a test result.

Such reflectometers are sometimes used for performing tests on a reagent test strip. In such a case, the test pads on the test strip may be incrementally tested to determine the presence of analytes in a liquid test sample absorbed into the test pads. Such systems may be used for performing urinalysis tests, as one example. That is, the level or presence of an analyte in a liquid test sample can be determined by causing a given test pad to absorb some of the liquid test sample, (e.g., a sample of urine) and then by reading associated reflectance values for the test pad with a reflectometer. Based on the spectral reflectance characteristics of the signal reflected by the test pad, the reflectometer determines the presence or level of the analyte in a given test pad. As an example, a test pad changes color to indicate the level or presence of the analyte in response to absorption of urine from a urine sample. The characteristics of a reflected signal are a function of the make-up and color of the test pad and the wavelength of the light source. Consequently, a change in color of a test pad causes a corresponding change in the characteristics of the reflected signal.

Test strips are typically produced according to industry accepted formats. In the case of urinalysis reflectometers, test strips can come in formats having different lengths, such as, for example, 3.25 inch lengths or 4.25 inch lengths. Within each format, a test strip is defined according to its configuration, i.e., the number, types and order of test pads included on the test strip. Generally, each test strip configuration is uniquely identified., Implicit in a test strip identification and/or confirmation, therefore, is the test strip format and the test pad configuration. As will be appreciated by those skilled in the art, such test pads may include, for example, pH, ketone, nitrite, and glucose test pads. In order for the reflectometer to produce valid results, the test strip must be identified by format and configuration, so that the reflectometer has a proper context to evaluate the received reflected signals, or reflectance values derived therefrom. That is, a reflectometer needs to know that a received reflected signal is produced by, for example, a glucose test pad or a ketone test pad.

Reagent cassettes can also tested using a reflectometer, in a manner very similar to that used for the test strip. Such reagent cassettes include a test region that provides visual indications of test results, similar the test pads of the test strips. The test region can produce a series of lines that embody the test results.

There is a variety of known ways that the test strip is identified to or by the reflectometer. In some reflectometers, an operator enters data into the reflectometer that indicates the identification of the test strip from a look up table, or chooses the identification from a set of predefined options. The same can be done for reagent cassettes. The reflectometer is then ready to process the test strip or cassette.

In typical reflectance-based instruments, such as reflectometers, light emitting diodes (LEDs) serve as sources of light, the reflections of which are then detected and evaluated. Each LED is specified to have a center wavelength, within some range. Depending on the application, the range can be relatively narrow, e.g., ±3 nanometers (nm). Wavelengths outside of this range can result in instrument errors or incorrect clinical results. Since there is no way to correct for LEDs having center wavelengths outside the specified range, presently, instrument makers are reliant on the relatively expensive process of sorting through large volumes of LEDs to find those that are within the specified range. Otherwise, reflectance-based instruments using less precise LEDs would be error prone.

SUMMARY OF THE INVENTION

In accordance with aspects of the present invention, provided is a system and method for correcting one or more reflectance values when a center wavelength of one or more light sources used to generate corresponding source light signals is different from a specified center wavelength for the one or more light sources. The present invention can be implemented as part of, or in conjunction with, any reflectance based system. And the light sources may be LEDs, or any other type of light source.

The system and method comprise defining, for each of the one or more light sources, a reference spectral distribution $\{L^*\}$ that is characteristic for the one or more light sources and comprised of reference light intensity values over a set of reference wavelengths. Also determined, for each of the one or more light sources, is a spectral distribution $\{L\}$ comprising actual light intensity values over the set of wavelengths. The actual reflectance R of a set of reflected signals is determined, e.g., through detection and measurement.

For a set of detectors used as part of the reflectance-based system, a set of detector sensitivity data {D} is also stored. And a set of high resolution reflectance values {r} is determined. The correction function uses {L}, {L*}, {r} and {D} to determine a correction factor. The correction factor is applied to the measured reflectance R to determine R*. Corrected reflectance R* is then used in the calculations and functions of the instrument that would typically use R.

Determining {r} may comprise measuring reflectance values $R_{IR}$ in the infrared range and determining $r_{IR}$ as a constant representing an average of $R_{IR}$ values, where each value in {r} equals the value of $(R/R_{IR}) \cdot r_{IR}$ at a corresponding wavelength. Additionally, the values of {r} can be determined at discrete wavelength intervals, where the intervals are sufficiently narrow, e.g., 1 nanometer, to provide close correlation to the actual wavelengths of the R values.

BRIEF DESCRIPTION OF THE DRAWINGS

The drawing figures depict preferred embodiments by way of example, not by way of limitations. In the figures, like reference numerals refer to the same or similar elements.

DETAILED DESCRIPTION OF THE PREFERRED EMBODIMENTS

In accordance with various aspects of the present invention, a wavelength correction function provides corrected reflectance values in a reflectance-base instrument. The correction is provided as a function of measured reflectance values and a predefined set of high resolution reflectance values established for the reflectance-based instrument implementing the wavelength correction function. Without wavelength corrections, reflectance-based instruments are intolerant of light sources, e.g., light emitting diodes (LEDs), having center wavelengths beyond narrowly specified wavelength ranges. Reflectance-based instruments having light sources with less reliable center wavelengths are relatively error prone.

Representative Reflectance-Based Instrument

Figure 1:
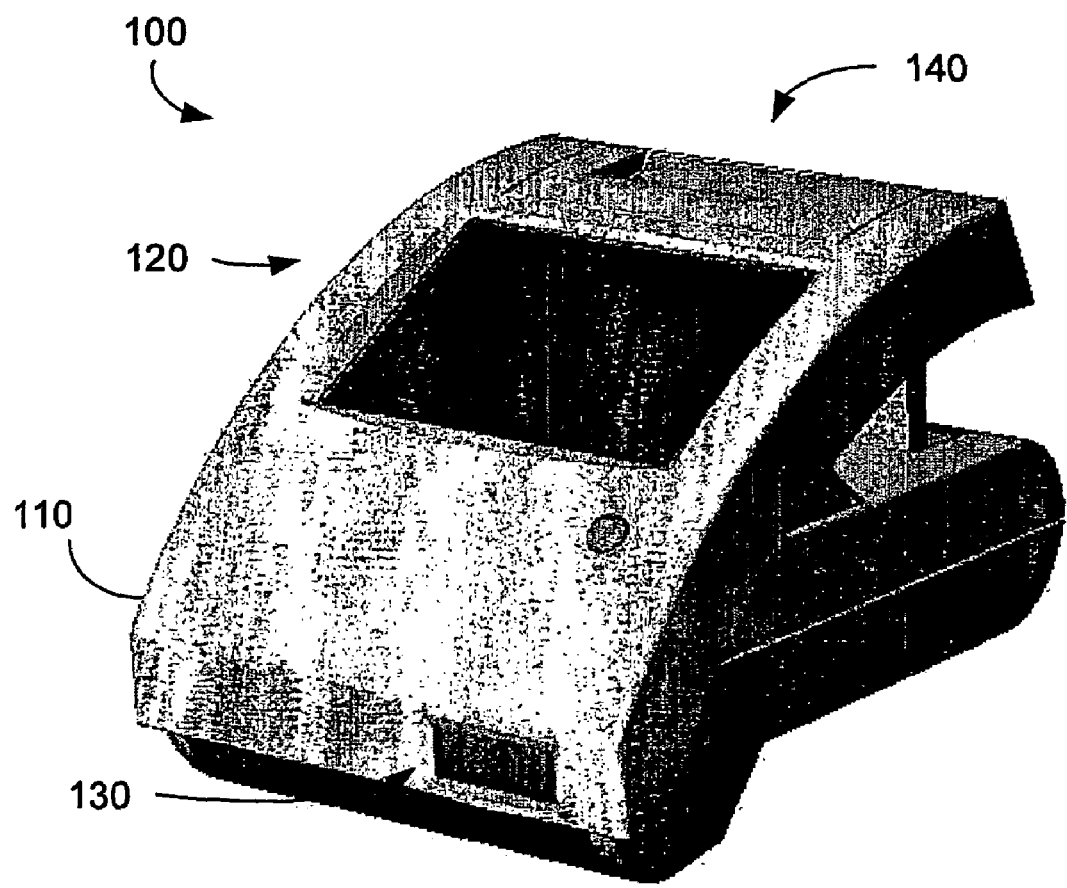
FIG. 1 is a perspective view of a reflectometer that may implement wavelength correction in accordance with the present invention.

FIG. 1 provides a perspective view of an embodiment of a reflectometer 100, as one example of a reflectance-based instrument, that may include functionality that implements the wavelength correction of the present invention. As will be appreciated by those skilled in the art, the present invention could be implemented in other reflectometers or reflectance-based instruments, so is not restricted to embodiments provided herein. Reflectometer 100 provides an input and output device in the form of a touch screen 120. An output port 140 may be provided as a means for printing a report (e.g., test or diagnostic report) to an operator or user of reflectometer 100. As will also be appreciated by those skilled in the art, other forms of input and output mechanisms may be used. For example, reflectometer 100 may be configured to couple, by wired or wireless means, to a personal computer, handheld computer, network, monitor, printer, audio/visual system or the like. A housing 110 houses the touch screen 120, as well as a variety of internal functional elements. An input port 130 is provided to facilitate insertion of one or more test strips or reagent cassettes (collectively, "test product(s)") via a carriage.

Figure 2:
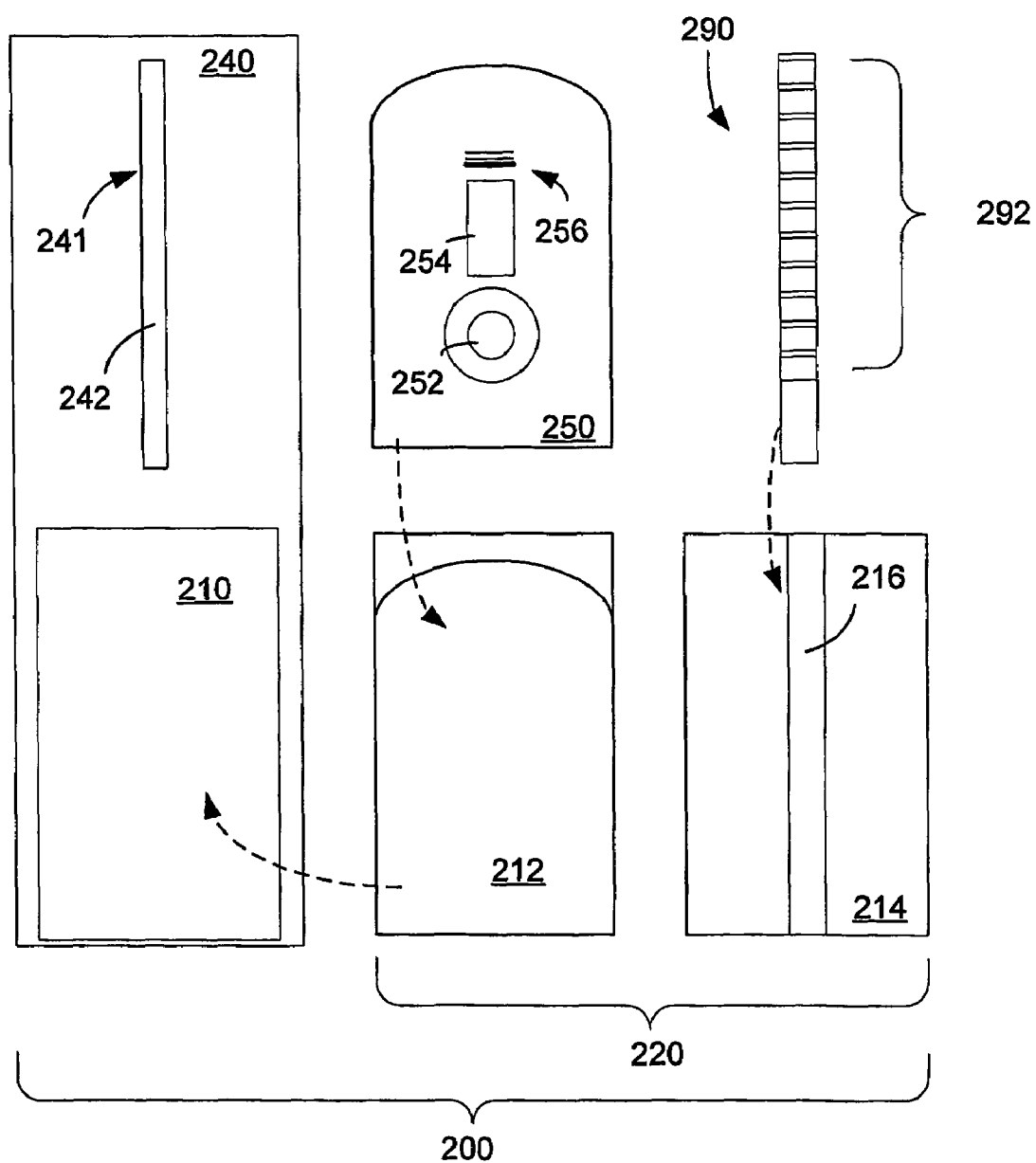
FIG. 2 is a view of a carriage used with the spectrometer of FIG. 1, including a view of a insert used with the carriage for accommodating various test strips.

Referring to FIG. 2, a collection of test product insertion components 200 for use with reflectometer 100 is shown. A carriage 240 is configured for insertion in input port 130 of the reflectometer 100, with a test product. Carriage 240 includes an insert region 210 within which a test product insert 220 configured to hold a test product (e.g., a reagent test strip 290 or cassette 250) may be placed. In the preferred form, insert 220 includes a first side 214 configured to hold the reagent test strip 290 within a slot 216. Representative test strip 290 includes a plurality of test pads 292, the configuration of which depends on the particular test strip type. Test strip 290 is positioned within slot 216 after the insert 220 is loaded into carriage 240 with side 214 available for testing. Carriage 240 may be configured to accommodate a test strip 290 of any of a variety of lengths, such as test strips of the 3.25" and 4.25" length formats, as examples.

A region of interest to be tested may include one or more of test pads 292. In order for the test pads 292 to be tested, those pads must be disposed to receive light from the LEDs and to reflect light for detection by light detectors, as described with respect to FIG. 3A and FIG. 3B below. Accordingly, in the embodiment of FIG. 2, test strip 290 is disposed within carriage 240 such that the test strip pads 292 are visible to such components.

Insert 220 may optionally include a second side 212 configured to accept reagent cassette 250. Such reagent cassettes are known in the art. For instance, reagent cassette 250 may be a disposable, single-use hCG immunoassay cassette for performing a pregnancy test. The reagent cassette 250, as with the test strip 290, includes a region of interest that may include a test area defined by a window 254 and also include identification markings, such as bar codes 256. The reagent test area is viewable and capable of being tested when the carriage is loaded into reflectometer 100.

The reagent cassette 250 has an opening or well 252 into which a body fluid sample, such as urine, is deposited. The fluid sample propagates to the test area defined by window 254. The reagent cassette test area comprises a test line area, reference line area and control line area, as is known in the art. Test results can take the form of one or more lines displayed in these areas. With introduction of a fluid sample, the reagent cassette test area may change color, for example, at least one colored stripe may appear in window 254.

As an example, the various components of FIG. 2 may take the form of those more fully described in co-owned and co-pending U.S. patent application Ser. No. 10/821,441, entitled TRAY ASSEMBLY FOR OPTICAL INSPECTION APPARATUS, filed Apr. 9, 2004.

Figure 3A:
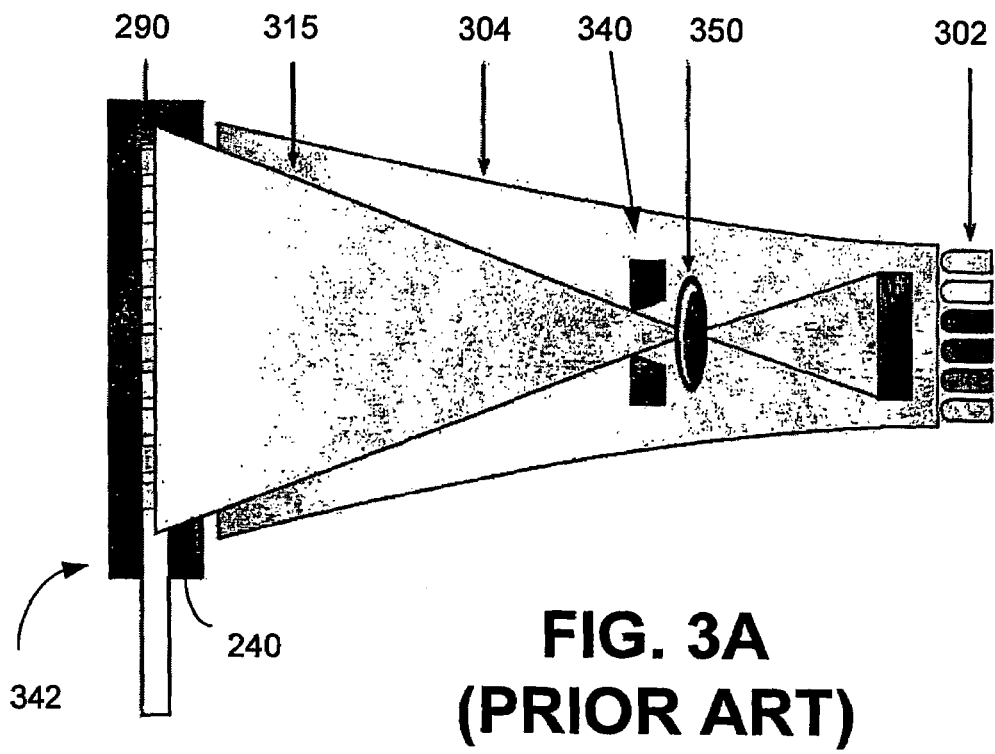
FIG. 3A and FIG. 3B are diagrams depicting a prior art arrangement of functional elements that can be used within the reflectometer of FIG. 1.
Figure 3B:
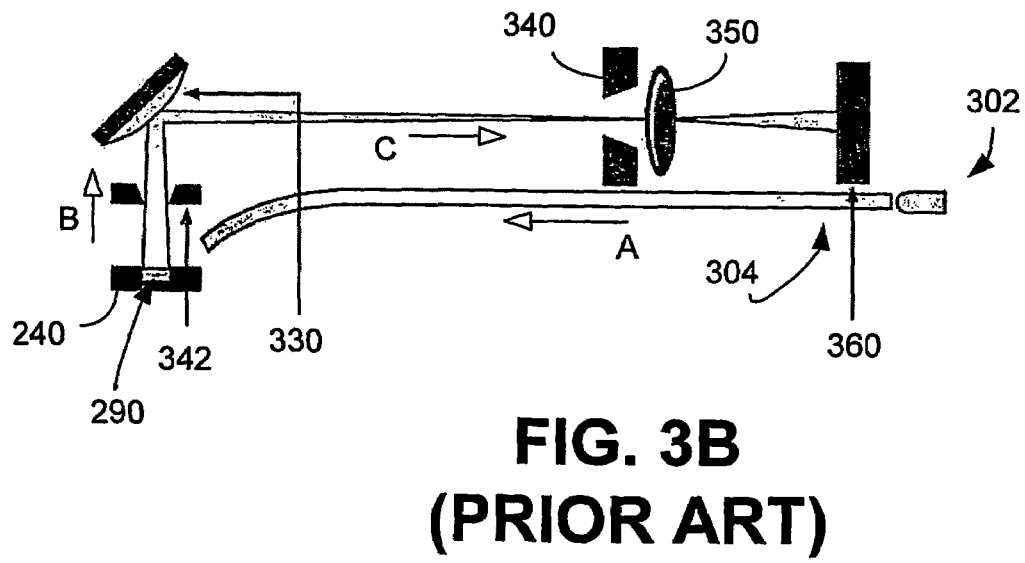

FIGS. 3A and 3B show two different views of a prior art embodiment of various functional elements that may be used for performing reflectance-based testing of a test product within reflectometer 100. A top view is shown in FIG. 3A and a side view is shown in FIG. 3B. As is shown in each of the figures, test signals are provided by transmitters 302. In this form, transmitters 302 are LEDs, preferably six, as shown in FIG. 3A, each of which transmits a different signal having a unique wavelength.

In this embodiment, the signals transmitted by the LEDs are:

1) LED 1: blue light at a center wavelength of about 470 nanometers (nm),
2) LED 2: green light at a center wavelength of about 525 nm,
3) LED 3: green light at a center wavelength of about 565 nm,
4) LED 4: red light at a center wavelength of about 625 nm,
5) LED 5: red light at a center wavelength of about 660 nm, and
6) LED 6: infrared (IR) radiation at a center wavelength of about 845 nm.

Test signals from LEDs 302 are transmitted through a guide 304 in the direction of arrow A. The test signals from guide 304 impinge on test strip 290 at an angle of about 45°, in the illustrative embodiment. In this embodiment, test strip 290 is housed within carriage 240. Light reflected from the test strip in the direction of arrow B passes through aperture 342, after which it impinges on a planar or convex mirror 330 (not shown in FIG. 3A), which redirects and focuses the reflected signals in the direction of arrow C. In this arrangement, due to the orientation of mirror 330, the path of the reflected signals takes about a 90° turn after leaving the test strip 290. The reflected signals propagating in the direction of arrow C pass through aperture 340 and converge at aspheric lens 350. Aspheric lens 350 focuses the reflected signals and the focused reflected signals continue to propagate in the direction of arrow C. The reflected signals impinge on detector 360. As will be appreciated by those skilled in the art, the shapes and arrangement of mirrors and lenses need not specifically conform to or be limited to those shown in the illustrative embodiment of FIGS. 3A and 3B.

As previously mentioned, detector 360 receives the reflected signals, translates them into an image comprised of data representing reflectance values associated with the test pads 292, and tests results therefrom. In this embodiment, detector 360 is a charge coupled device (CCD) comprised of a matrix of 2048 pixels configured to receive the reflected signals. Data from the reflected signals are recorded pixel-by-pixel as the reflectance values. Pixel data are grouped and associated with individual pads on the test strip 290. As a result, reflectance values for each pad of the test strip 290 are stored.

Center Wavelength Correction

Each LED used in a reflectometer is rated at or identified as having a predefined spectral distribution that includes a center wavelength, as noted with LEDs 302 above. Wavelengths within a certain range of the center wavelength are typically considered useful, i.e., not prone to causing errors. Consequently, a useful portion of the spectral distribution for each LED can be defined as the center wavelength±a range value.

Within a reflectometer, results with respect to reagents are determined from the reflection of light from the source LEDs by the test product. The reflected light, referred to as reflectance, is detected by detectors, as discussed above with respect to the reflectometer 100 of FIG. 1 and FIGS. 3A and 3B. The detected reflectance values are a function of the center wavelengths of the source LEDs. In prior systems, if an LED's center wavelength was outside of the presumed ±3 nm, errors likely occurred. The likelihood of an error has also been somewhat dependent on the slope of curve of the spectral distribution for the given reagent, since some are more immune to variability in the center wavelength than others. For instance, with a reagent having a fairly flat slope across a range of center wavelengths that includes the actual center wavelength, such as Occult Blood, being off-center would have negligible effect, typically. But with reagents having relatively high slopes, such as pH and Glucose, an off-center wavelength could produce an error condition within the instrument.

Since LEDs are typically purchased in volume, it is impractical to measure the range of each LED. For example, a set of one thousand LEDs could be rated or indicated as having a center wavelength of 470 nm. Sampling various LEDs in the set could show that the estimated average center wavelength is 471 nm, not 470 nm. This sampling could also show that the width of the useful range for this set of LEDs is about 14 nm, not 6 nm, i.e., not the specified range of ±3 nm. Using LEDs 302 above as examples, with a set of LEDs corresponding to each LED above, the center wavelength and range of the sets of LEDs could be characterized as follows:

1) LED 1: 471+6/−7 nm
2) LED 2: 525+6/−7 nm
3) LED 3: 572+2/−3 nm
4) LED 4: 621+3/−3 nm
5) LED 5: 652+6/−7 nm
6) LED 6: 843+5/−5 nm

In prior systems, LEDs having center wavelengths outside the specified ±3 nm range would not be used. However, with the center wavelength correction aspects of the present invention, adjustments (or "corrections") can be made to the measured reflectance values to accommodate center wavelengths, within ranges of at least about ±8 nm.

For each LED a reference spectral distribution (or LED emission intensity) is determined. The reference spectral distribution for each LED is designated as array $\{L^*\}$, where individual members of $\{L^*\}$ give the intensity of the light output of the LED at different wavelengths. Therefore, for each of LEDs 302 above, there will be an array $\{L^*\}$: for LED 1, $\{L^*\}=\{L_{470}^*\}$; for LED 2, $\{L^*\}=\{L_{525}^*\}$; and so on. Array $\{L^*\}$ is stored in memory for use by a wavelength correction function in determining the appropriate correction factor to be used in correcting the actual measured output spectral distribution $\{L\}$ for each LED. The actual spectral distribution of light output by each LED used in a reflectometer is assumed to be unknown in advanced, and are saved in an array $\{L\}$, comprised of measured L values for each LED. So, as with $\{L^*\}$, there will be an array for each LED: for LED 1, $\{L\}=\{L_{470}\}$; for LED 2, $\{L\}=\{L_{525}\}$; and so on.

Figure 4:
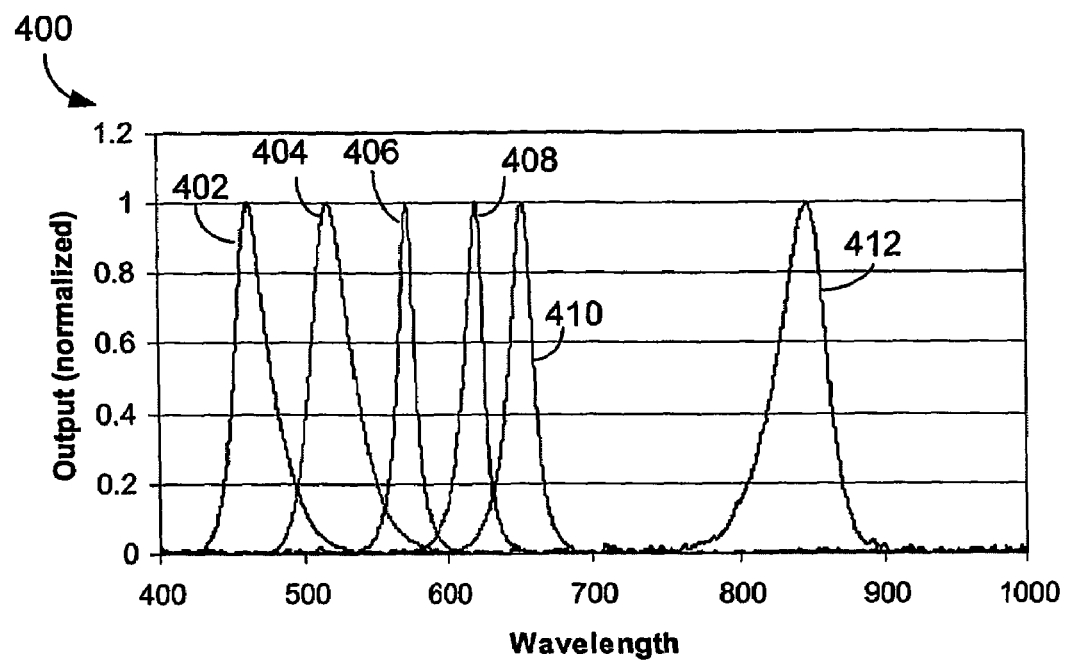
FIG. 4 is a graph of representative plots of LED spectral distributions for each of the six LEDs of the reflectometer of FIG. 1 and FIGS. 3A-B, and used in the wavelength correction of FIG. 5.

FIG. 4 is a graph 400 showing representative plots of LED distributions $\{L^*\}$ for each of the six LEDs, such as LEDs 302 above. In graph 400 wavelength in nanometers is represented on the horizontal axis and output intensity is represented on the vertical axis. Plot 402 corresponds to LED 1, having a center wavelength of about 470 nm. Plot 404 corresponds to LED 2, having a center wavelength of about 525 nm. Plot 406 corresponds to LED 3, having a center wavelength of about 565 nm. Plot 408 corresponds to LED 4, having a center wavelength of about 625 nm. Plot 410 corresponds to LED 5, having a center wavelength of about 660 nm. And plot 412 corresponds to LED 6, having a center wavelength of about 845 nm.

In accordance with aspects of the present invention, an instrument that has a reference spectral distribution of array {L*} can give rise to corrected reflectance values R*. But an array of the actual spectral distribution {L} of the LEDs gives rise to reflectance values R, not R*, since measured reflectance is a function of measured array {L}. That is, without any wavelength correction, R would be the reflectance measured, reported, and used by the instrument in all equations and calculations. Depending on the center wavelength, using R could yield an error, while using R* would not. The objective of wavelength correction function is, therefore, to provide a mechanism for determining R* for the instrument, even though the actual LED output distribution in that instrument is {L}, not {L*}, and the measured reflectance values are R. Once R* is determined for each LED, R* is used in the functions and equations for determining reflectance-based results. These functions and equations are known in the art, so are not discussed in detail herein.

In accordance with one aspect of the present invention, a correction function c is determined to provide as means of converting R to R*. The observed reflectance R and the wavelength corrected reflectance R* are associated with a single measurement of reflectance at a single wavelength on a single instrument. Their relationship can be expressed according to Equation 1:

$$R^* = R \cdot c(R) \quad (1)$$

alternatively, $$c(R) = R^*/R \quad (1)$$

Therefore, R* is the wavelength corrected reflectance, obtained by multiplying the observed reflectance R by c. And correction function c(R) can also be expressed as a ratio of corrected reflectance value R* divided by measured reflectance value R, for a given LED.

Figure 5:
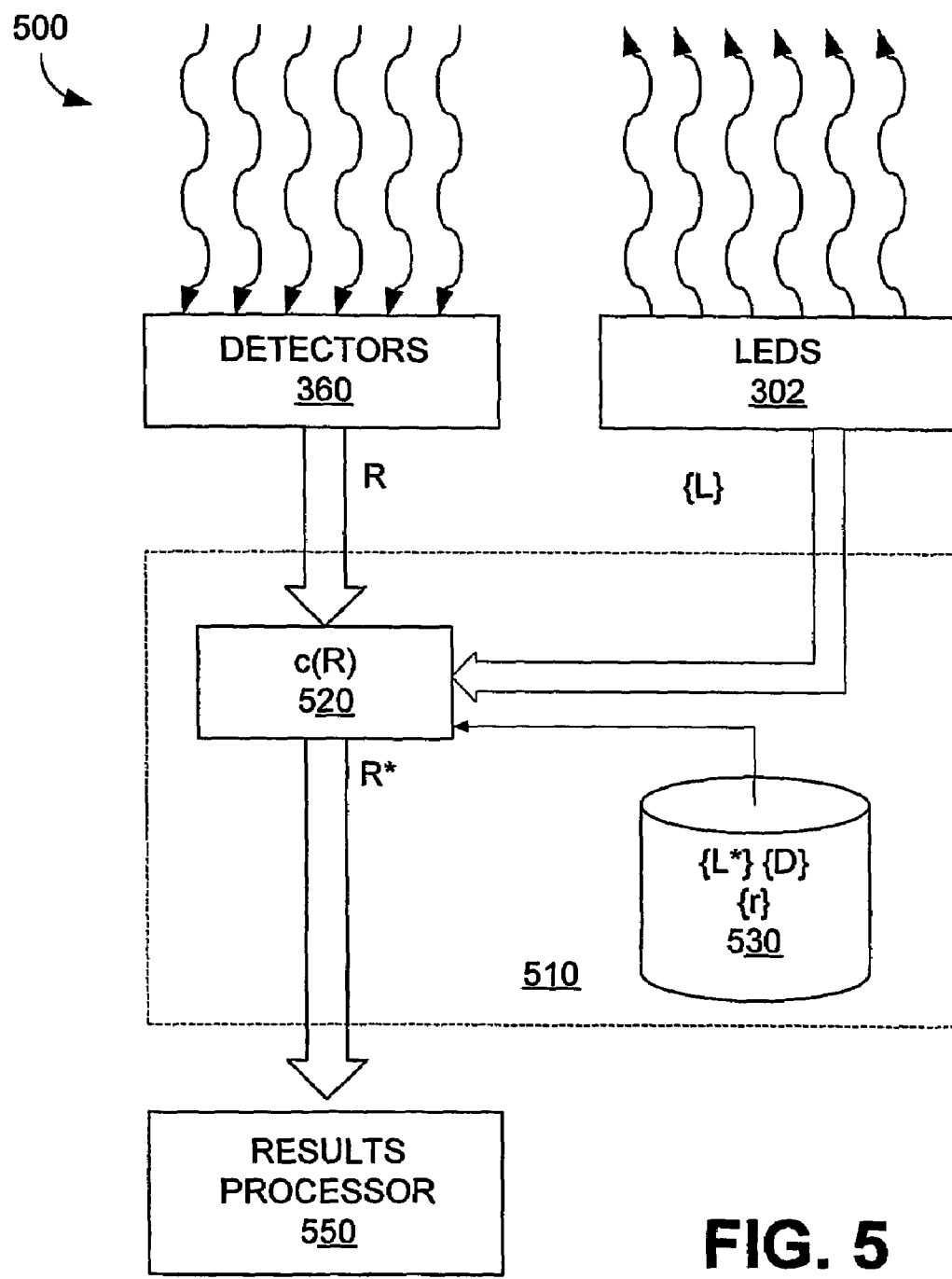
FIG. 5 is a block diagram depicting wavelength correction in accordance with aspects of the present invention, within the context of the reflectometer of FIG. 1, FIG. 3A and FIG. 3B.

Equation 1, and the correction function is demonstrated in FIG. 5, which is a block diagram 500 depicting wavelength correction in accordance with aspects of the present invention, within the context of the reflectometer of FIG. 1, FIG. 3A and FIG. 3B. As is shown also in FIGS. 3A and 3B, the LEDs 302 generate light toward a test product, and the reflected light is received by detectors 360. For each instrument, LEDs 302 yield spectral distribution array {L} and the actual, measured reflectance from the detectors is represented by R. In accordance with aspects of the present invention, the wavelength correction function 520, represented as c(R), outputs the corrected reflectance R*, which is then used by the processor and functions for producing results—given the particular application of the instrument. The correction function 520 determines a correction factor, either from inputs {L*}, {D} and {r} or, alternatively, from a table of predetermiined c(R) values—all of which is discussed in further detail below. The correction factor is combined with the measured reflectance R to determine R*. As will be appreciated by those skilled in the art, the correction function 520 could be implemented in software, firmware, hardware, or any combination thereof.

More specifically, Equation 1 can also be expressed as follows:

$$R^* = R \cdot c(R/R_{IR} \cdot r_{IR}) \quad (2)$$

where $c(R/R_{IR} \cdot r_{IR})$ is an alternative way to express the correction function, which does not rely on R*.

$R_{IR}$ is the measured reflectance in the infra red (IR) range and $r_{IR}$ is a constant representing the average IR reflectance. In the IR, the reagents measured typically converge and have a near-zero slope, so that it becomes possible to assign a constant reflectance value to reflectance readings in the IR. The constant IR reflectance is thus independent of concentration and wavelength (as long as the wavelength is within the specified IR range). For purposes herein, from these constant IR reflectance values $r_{IR}$ a high resolution reference reagent spectrum {r} is defined, where each value of r in array {r} equals the corresponding value of $(R/R_{IR}) \cdot r_{IR}$.

In addition to the high resolution reference reagent spectrum {r}, other factors could play a significant role in determining the measured reflectance R in a reflectometer. Previous modeling has shown that an LED spectral emission {L} and detector sensitivity {D} weighted average of high resolution reflectance spectra provides an excellent model of the measured reflectance R. Accordingly, reflectance R can be calculated using the following equation:

$$R = \sigma L_i \cdot r_i \cdot D_i / \sigma L_i \cdot D_i \quad (3)$$

where $L_i$ are the elements of array {L} for the LED, $r_i$ are the elements of an array {r} of high resolution reflectance values for a specific reagent at a specific concentration, and $D_i$ are elements of the array {D} of detector sensitivities.

Using the same principles, a similar equation can be written for R*:

$$R^* = \sigma L^*_i \cdot r_i \cdot D_i / \sigma L^*_i \cdot D_i \quad (4)$$

where $L^*_i$ are the elements of array {L*} for the LED reference spectral outputs, which are known. The reference LED spectral distributions {L*} are generally chosen to have a shape characteristic of the expected distributions of array {L}.

Equation 1 above can be solved for by substituting Equation 3 for R and Equation 4 for R*, as follows:

$$c(R) = \frac{\left(\frac{\sum L^*_i r_i D_i}{\sum L^*_i D_i}\right)}{\left(\frac{\sum L_i r_i D_i}{\sum L_i D_i}\right)} \quad (5)$$

Figure 6:
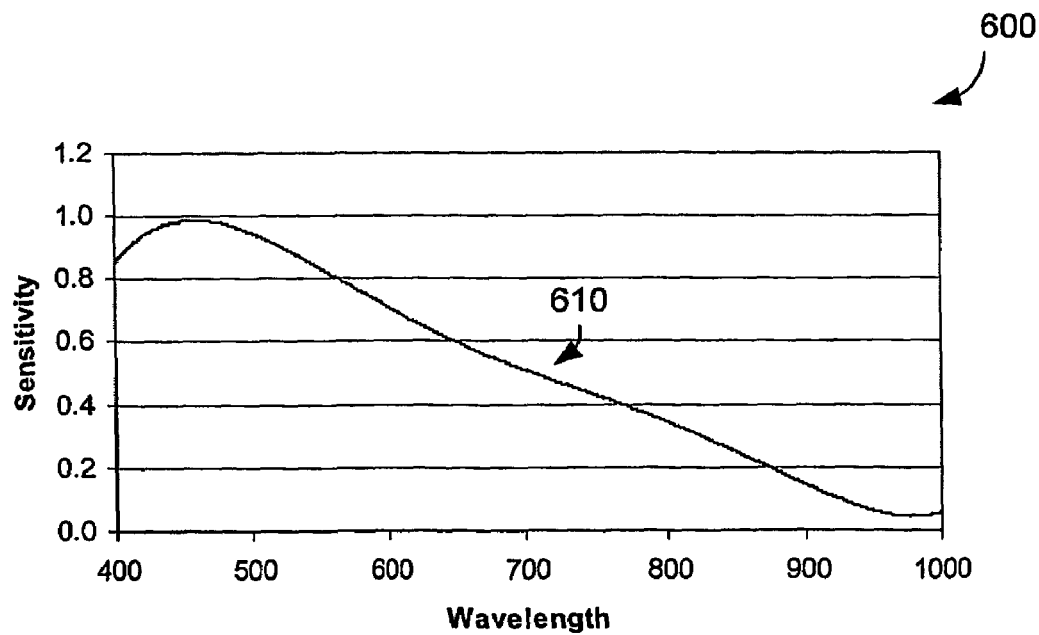
FIG. 6 is a representative plot of detector sensitivity for CCDs of the reflectometer of FIG. 1 and FIGS. 3A-B and used in the wavelength correction of FIG. 5.

The values of all variables can be determined. All values of {L*} are known, as are all values of array {D}. In Equation 5 it is generally appropriate to use the nominal detector sensitivity curve {D} of the detectors, which is typically supplied by the detector vendor. A representative plot 600 of {D} is provide in FIG. 6, which provides a plot for CCDs as used in reflectometer 100. In FIG. 6, wavelength is represented on the horizontal axis and detector sensitivity is represented on the vertical axis.

The high resolution reflectance values of array {r} provide reference reflectance values of the reagent at specific times, for specific analyte concentrations, and at narrow wavelength intervals, e.g., typically less than 1 nm. The instrumentally determined reflectance measurements R and wavelength corrected reflectance values R* use an LED as the light source, having typical 20-40 nm bandwidths, which are much broader than the interval of the high resolution measurements, so the 1 nm increments are sufficiently narrow to provide granularity within the light source bandwidths.

High resolution reflectance values {r} are generally available at color block levels, represented as k. As will be appreciated by those skilled in the art, color block levels are typically predefined for reagent test products. For example, if a given test pad on a test strip turns a certain, predefined color, the test may be determined to be positive or negative, as the case may be. The color indicates a concentration of the analyte, if present. In the measurement of high resolution reflectance, measurements are made with respect to those concentrations which correspond to the predefined color blocks.

For each wavelength of each color block k of each analyte, $R_k$ and $c(R_k)$ can be determined. The k designation is used to indicate the different color blocks for the different reagents. For example, there are 2 blocks for Nitrite and 5 color blocks for Glucose. When the measured reflectance at a specific wavelength of a specific analyte is $R_k$, then the correction factor is $c(R_k)$.

Figure 7A:
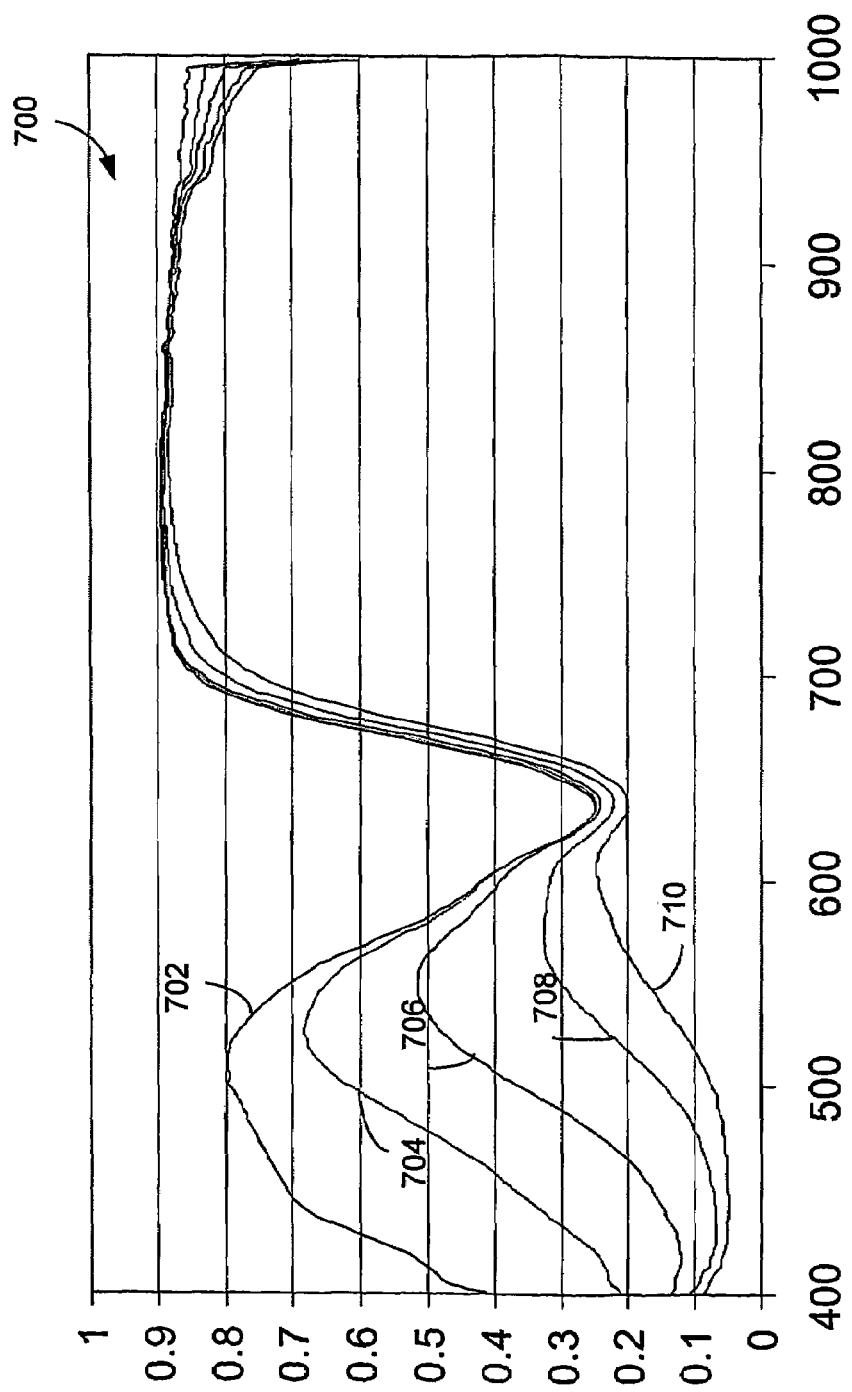
FIG. 7A and FIG. 7B are representative plots of reference high resolution reflectance values at various color block levels for Glucose and pH, used in the wavelength correction of FIG. 5.
Figure 7B:
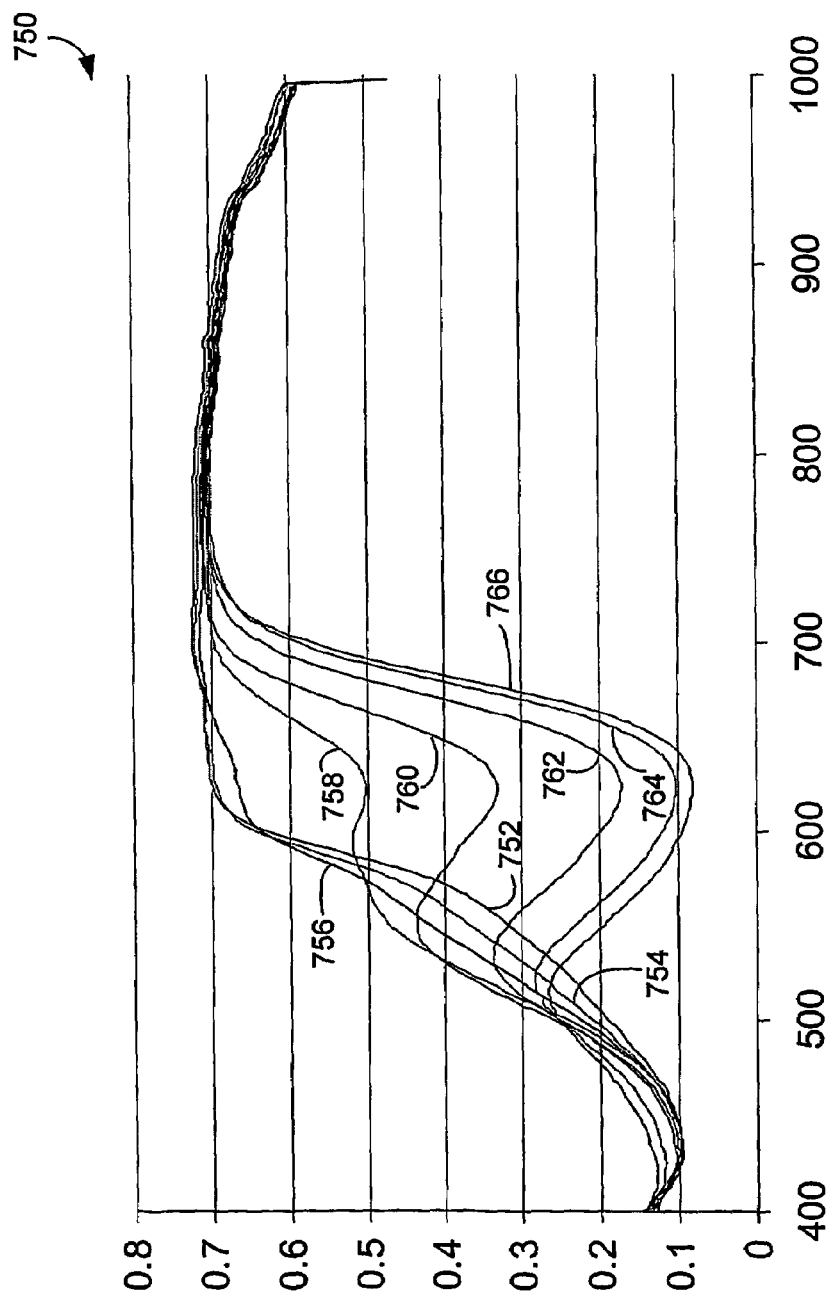

The high resolution reflectance values of array {r} at the color block levels are generally measured at or near the read times which will be implemented in the production instrument, e.g., production reflectometers. Representative plots of {r} at various color block levels for Glucose (plot 700) and pH (plot 750) are provided in FIGS. 7A and 7B, respectively. In FIGS. 7A and 7B wavelength is represented on the horizontal axis and reflectance (which is $\leq 1$) is represented on the vertical axis. For each color block there is a curve. In plot 700 for Glucose, curve 702 represents $r_1$ for color block 1, curve 704 represents $r_2$ for color block 2, curve 706 represents $r_3$ for color block 3, curve 708 represents $r_4$ for color block 4, and curve 710 represents $r_5$ for color block 5. Table 1 below also shows corresponding data for $r_1$-$r_5$. Similarly, in plot 750 for pH, curves 752, 754, 756, 758, 760, 762, 764, and 766 represent $r_1$-$r_8$ for color blocks 1-8, respectively.

Options For Determining c(R)

There are at least two options for determining c(R). A first option is to measure the actual distribution {L} of the LEDs used in the instrument (e.g., reflectometer 100) and perform the calculations required by Equation 5. Since all other variables are known, or can be determined from available information, satisfying for {L} is all that is required to determine c(R).

A second option is to calculate Equation 5 at fixed LED center wavelength intervals, and in the production instrument use those $c(R_k)$ values for which the computed center wavelength most closely matches the measured, or actual, center wavelength. These values can be calculated and entered into a table, such as Table 1 below. However, this option will not suffice in all circumstances, but will work well in some. This is because the second option assumes that the shapes of the spectral distributions of the various LEDs of the production instrument play a small role in the correction factors. If $c(R_k)$ is not a function of R, then there will not be a predictable value of c(R) for each R. This has been observed for pH, where reflectance goes up, then down with pH.

Figure 8A:
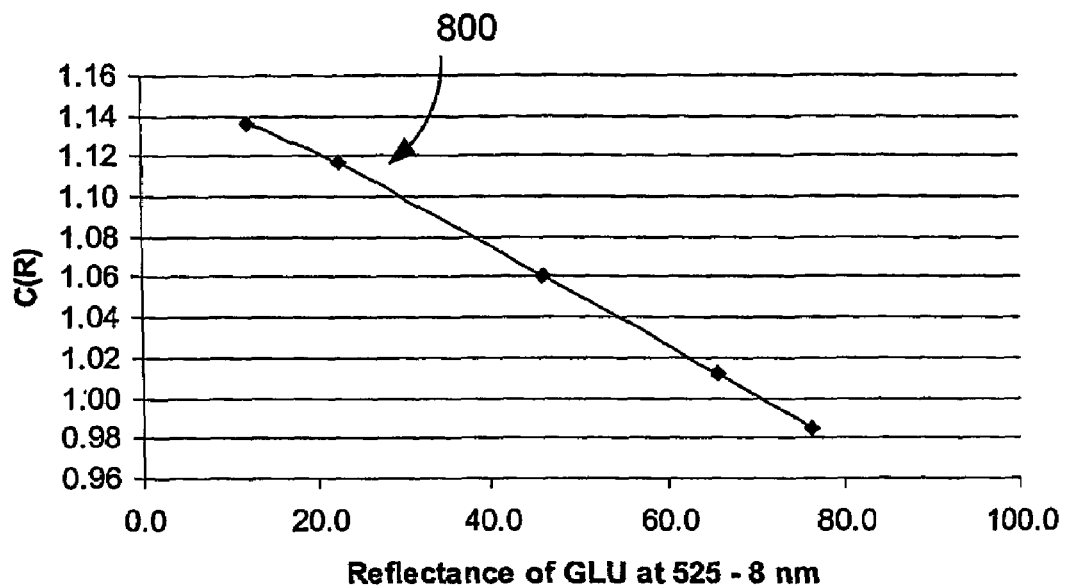
FIG. 8A and FIG. 8B are representative plots of wavelength correction values at various color block levels for Glucose and pH, used in the wavelength correction of FIG. 5.
Figure 8B:
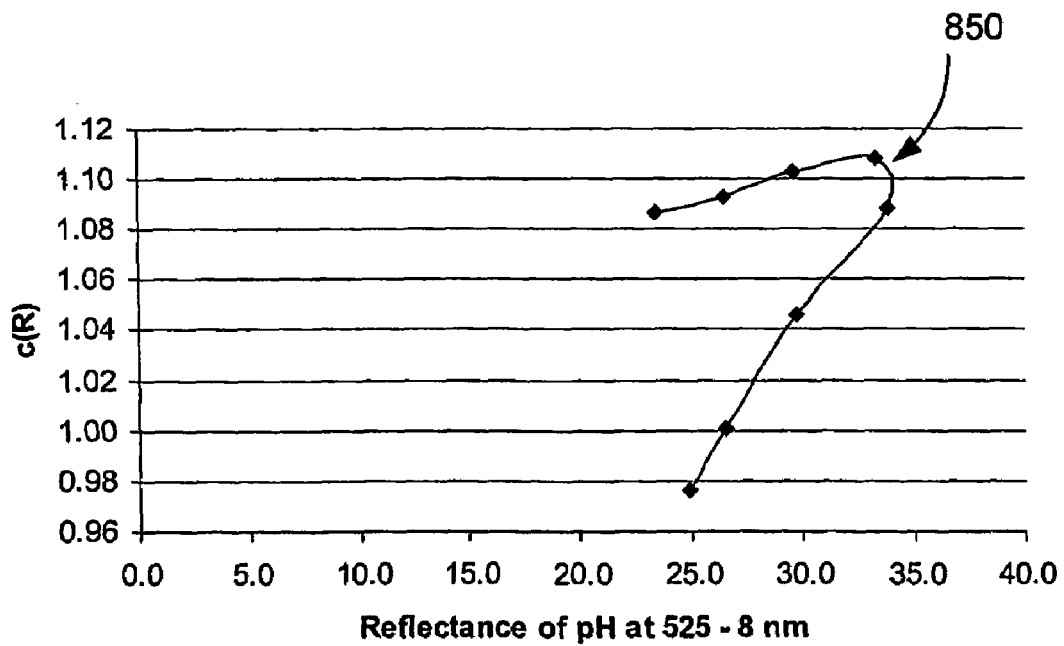

For example, wavelength sensitivity for Glucose and pH is shown in the representative plots 800 and 850 of FIGS. 8A and 8B, respectively. In FIGS. 8A and 8B reflectance is represented on the horizontal axis and c(R) is on the vertical axis. The Glucose plot 800 shows that the c(R) curve changes slowly with R, allowing linear interpolation to be a good method of approximating between known $c(R_k)$ values (see Table 1 below). However, because of the unique spectra of pH caused by its dual indicators, the plot 850 of the c(R) curve for pH is not a function of R.

Using this second option, any c(R) curve that is not a function of R can be treated as a special case. For example, pH is a special case. But it has been identified that only a portion of curve 850 was needed in solving Equation 5. This allows elimination of about half of the points. In doing so, a functional relationship between c and R can be obtained.

Using this process, functional $c(R_k)$ tables can be calculated for all color block levels of all analytes over a range of about ±8 nm from the center wavelength of the reference LED distribution {L*}—here in intervals of 1 nm. This is substantially equivalent to a +1 nm sort of the LEDs by center wavelength.

In the preferred form, wavelength correction function c for each LED is tabulated every 1 nm in LED wavelengths. Table 1 is a sample for the analyte Glucose for wavelengths between 468 nm and 479 nm. Here, the range of k is 1 to 5, thus there are reference reflectance values in {r} represented in Table 1 as r1-r5. There is one reflectance value for each color block. Accordingly, for each reflectance value, since c is a function of R, there is a c(r) corresponding to each r value.

TABLE 1

| Wavelength | c(r1) | c(r2) | c(r3) | c(r4) | c(r5) | r1 | r2 | r3 | r4 | r5 |
|---|---|---|---|---|---|---|---|---|---|---|
| 468 | 1.0064 | 1.0304 | 1.0460 | 1.0389 | 1.0218 | 75.1279 | 48.9656 | 25.0088 | 10.2199 | 5.9157 |
| 469 | 1.0042 | 1.0201 | 1.0305 | 1.0261 | 1.0147 | 74.9655 | 48.4772 | 24.6384 | 10.0932 | 5.875 |
| 470 | 1.0021 | 1.0100 | 1.0151 | 1.0131 | 1.0075 | 74.8069 | 47.9959 | 24.2720 | 9.9655 | 5.8329 |
| 471 | 1.0000 | 1.0000 | 1.0000 | 1.0000 | 1.0000 | 74.6521 | 47.5222 | 23.9098 | 9.8369 | 5.7896 |
| 472 | 0.9980 | 0.9902 | 0.9850 | 0.9869 | 0.9923 | 74.5000 | 47.0551 | 23.5517 | 9.7075 | 5.7451 |
| 473 | 0.9960 | 0.9805 | 0.9702 | 0.9736 | 0.9844 | 74.3512 | 46.5956 | 23.1981 | 9.5775 | 5.6993 |
| 474 | 0.9940 | 0.9710 | 0.9556 | 0.9604 | 0.9763 | 74.2055 | 46.1434 | 22.8491 | 9.4471 | 5.6523 |
| 475 | 0.9921 | 0.9616 | 0.9412 | 0.9471 | 0.9680 | 74.0628 | 45.6989 | 22.5049 | 9.3163 | 5.6042 |
| 476 | 0.9902 | 0.9524 | 0.9270 | 0.9338 | 0.9595 | 73.9230 | 45.2619 | 22.1656 | 9.1853 | 5.555 |
| 477 | 0.9884 | 0.9434 | 0.9131 | 0.9204 | 0.9508 | 73.7860 | 44.8325 | 21.8314 | 9.0543 | 5.5047 |
| 478 | 0.9866 | 0.9345 | 0.8993 | 0.9071 | 0.9419 | 73.6518 | 44.4109 | 21.5023 | 8.9233 | 5.4534 |
| 479 | 0.9848 | 0.9258 | 0.8858 | 0.8938 | 0.9329 | 73.5205 | 43.9971 | 21.1786 | 8.7925 | 5.4011 |

In practice, tables like that of Table 1 can be provided for all analytes, and at all wavelengths, in 1 nm increments, for each LED. Although there is a priori knowledge of only the color block reflectance values {r} and associated reference reflectance distribution values {L*}, reflectance values between those in the tables must also be accommodated, such that a corresponding c(R) can be reliably determined.

There are at least three ways for approximating the correction factor c(R) associated with a specific reflectance R using tabulated data, such as that provided in Table 1.

1) Round the measured reflectance to the closest tabulated value and use the associated correction value.
2) Interpolate when the measured reflectance value lies between adjacent points within the table, but use the extreme tabulated correction factor if the value lies outside the table.
3) Interpolate within the table, but extrapolate outside the table.

For some analytes, there is a significant change in the correction factor between points. Therefore, option 1 is typically not preferred. The decision between options 2 and 3 rests on the question of whether it is expected that the correction coefficients level off or continues to change beyond the ends of the measured reflectance range. For the negative levels, there will not be any change because the negative is already at the extreme of low concentration values. For the positive level, most analytes are nearing the maximum change in reflectance. Thus, option 2 is generally preferred.

Regardless of whether c(R) is determined using option 1 or option 2, Equation 1 is used to find R*. Equation 1 provides:

$$R^* = R \cdot c(R) \qquad (1)$$

R is measured by the instrument, as is typically done. c(R) is determined as provided above, thus R* is easily calculated. Once calculated, R* is the reflectance value used in the typical instrument calculations, which ordinarily use R. Accordingly, an error condition that would have occurred using R is avoided, and a proper result is achieved with R* determined using the wavelength correction function in accordance with the present invention.

While the foregoing has described what are considered to be the best mode and/or other preferred embodiments, it is understood that various modifications may be made therein and that the invention or inventions may be implemented in various forms and embodiments, and that they may be applied in numerous applications, only some of which have been described herein. As used herein, the terms "includes" and "including" mean without limitation. It is intended by the following claims to claim any and all modifications and variations that fall within the true scope of the inventive concepts.

What is claimed is:

1. A method of correcting one or more reflectance values when a center wavelength of one or more light sources used to generate corresponding light signals is different from a specified center wavelength for the one or more light sources, the method comprising the steps of:
   A. defining, for each of the one or more light sources, a reference spectral distribution {L*} that is characteristic of the one or more light sources and composed of reference light intensity values over a set of reference wavelengths;
   B. defining, for each of the one or more light sources, a spectral distribution {L} comprising actual light intensity values over the set of wavelengths;
   C. determining the actual reflectance R of a set of reflected signals;
   D. defining a set of detector sensitivity data {D} corresponding to the set of detectors receiving the set of reflected signals;
   E. determining high resolution reflectance values {r};
   F. determining a correction factor as a function of {L}, {L*}, {r} and {D}; and
   G. applying the correction factor to R to determine R*.

2. The method of claim 1, wherein determining the correction factor in step F is valid up to a range of at least about ±8 nanometers around the specified center wavelength.

3. The method of claim 1, wherein the one or more light sources comprise LEDs.

4. The method of claim 1, wherein at least one of the one or more light sources is an infrared light source and determining {r} in step E comprises measuring reflectance values $R_{IR}$ in the infrared range and determining $r_{IR}$ as a constant representing an average of $R_{IR}$, where each value in {r} equals the value of $(R/R_{IR}) \cdot r_{IR}$ at a corresponding wavelength.

5. The method of claim 4, wherein the values of {r} are determined at discrete wavelength intervals.

6. The method of claim 1, wherein the one or more light sources and set of detectors comprise part of a reflectometer.

7. The method of claim 1, wherein determining a correction factor as a function of {L}, {L*}, {r} and {D} comprises determining a correction factor $$c(R) = \left( \frac{\sum L_i * r_i D_i}{\sum L_i * D_i} \right) \bigg/ \left( \frac{\sum L_i r_i D_i}{\sum L_i D_i} \right).$$

8. A center wavelength correction system configured to correct one or more reflectance values when a center wavelength of one or more light sources used to generate corresponding light signals is different from a specified center wavelength for the one or more light sources, the system comprising:
   A. a spectral distribution module configured to determine, for each of the one or more light sources, a spectral distribution {L} comprising actual light intensity values over the set of wavelengths;
   B. a reflectance module configure to determine actual reflectance R from a set of reflected signals;
   C. at least one storage device comprising:
      1) for each of the one or more light sources, a reference spectral distribution {L*} that is characteristic of the one or more light sources and composed of reference light intensity values over a set of reference wavelengths;
      2) high resolution reflectance values {r}; and
      3) detector sensitivity data {D} corresponding to the set of detectors receiving the set of reflected signals;
   D. a correction function module configured to determine a correction factor at a given wavelength as a function of {L}, {L*}, {r} and {D} and to apply the correction factor to R to determine R*.

9. The system of claim 8, wherein the correction function module is configured to determine the correction factor within a range of at least about ±8 nanometers around the specified center wavelength.

10. The system of claim 8, wherein the one or more light sources comprise LEDs.

11. The system of claim 8, wherein at least one of the one or more light sources is an infrared light source and the correction function is configured to determine {r} as a function of measured reflectance values $R_{IR}$ an the infrared range and a constant $r_{IR}$ that represents an average of $R_{IR}$, where each value in {r} equals the value of $(R/R_{IR})r_{IR}$ at a corresponding wavelength.

12. The system of claim 11, wherein the values of {r} are determined at discrete wavelength intervals.

13. The system of claim 8, wherein the one or more light sources and set of detectors comprise part of a reflectometer.

14. The system of claim 8, wherein the correction function module is configured to determine a correction factor $$c(R) = \left(\frac{\sum L_i * r_i D_i}{\sum L_i * D_i}\right) \Big/ \left(\frac{\sum L_i r_i D_i}{\sum L_i D_i}\right).$$

15. A wavelength correction means for correcting one or more reflectance values when a center wavelength of one or more light sources used to generate corresponding light signals is different from a specified center wavelength for the one or more light sources, the system comprising:
   A. a spectral distribution means for determining, for each of the one or more light sources, a spectral distribution {L} comprising actual light intensity values over the set of wavelengths;
   B. a reflectance means for determining actual reflectance R from a set of reflected signals;
   C. at least one storage means far storing:
      1) for each of the one or more light sources, a reference spectral distribution {L} that is characteristic of the one or more light sources and composed of reference light intensity values over a set of reference wavelengths;
      2) high resolution reflectance values {r}; and
      3) detector sensitivity data {D} corresponding to the set of detectors receiving the set of reflected signals;
   D. a correction function means for determining a correction factor at a given wavelength as a function of {L}, {L*}, {r} and {D} and to apply the correction factor to R to determine R*.

16. The means of claim 15, wherein the correction function means includes means for determining the correction factor within a range of at least about ±8 nanometers around the specified center wavelength.

17. The means of claim 15, wherein the one or more light sources comprise LEDs.

18. The system of claim 15, wherein at least one of the one or more light sources is an infrared light source and the correction function means includes means for determining {r} as a function of measured reflectance values $R_{IR}$ in the infrared range and a constant $r_{IR}$ that represents an average of $R_{IR}$, where each value in {r} equals the value of $(R/R_{IR})$ $r_{IR}$ at a corresponding wavelength.

19. The system of claim 18, wherein the correction function means includes means for determining values of {r} at discrete wavelength intervals.

20. The system of claim 15, wherein wavelength correction means comprises a portion of a reflectometer means.

21. The wavelength correction means of claim 15, wherein the correction function means is configured to determine a correction factor $$c(R) = \left(\frac{\sum L_i * r_i D_i}{\sum L_i * D_i}\right) \Big/ \left(\frac{\sum L_i r_i D_i}{\sum L_i D_i}\right).$$

22. A reflectometer comprising:
   A. a set of light sources;
   B. a set of detectors;
   C. a reflectance assembly configured to direct light signals from the set of light sources onto a test product and to direct light signals reflected from the test product onto the set of detectors;
   D. at least one storage device configured to store a reference spectral distribution {L*}, a set of high resolution reflectance values {r}, a set of detector sensitivity data {D} corresponding to the set of detectors, a measured spectral distribution {L} corresponding tote set of light sources, and a set of measured reflectance values R; and
   E. a correction function module for determining a correction factor at a given wavelength as a function of {L}, {L*}, {r} and {D} and to apply the correction factor to R to determine R*.

23. The reflectometer of claim 22, wherein the set of light sources comprises a set of LEDs.

24. The reflectometer of claim 22, wherein the correction function module is configured to determine a correction factor $$c(R) = \left(\frac{\sum L_i * r_i D_i}{\sum L_i * D_i}\right) \Big/ \left(\frac{\sum L_i r_i D_i}{\sum L_i D_i}\right).$$

25. A wavelength correction module, in a reflectance-based system comprising a set of light sources, a set of detectors, and a reflectance assembly configured to direct light signals from the set of light sources onto a test product and to direct light signals reflected from the test product onto the set of detectors, the wavelength correction module comprising:
   A. at least one storage device configured to store a reference spectral distribution {L*}, a set of high resolution reflectance values {r}, a set of detector sensitivity data {D} corresponding to the set of detectors, a measured spectral distribution {L} corresponding to the set of light sources, and a set of measured reflectance values R; and
   B. a correction function module for determining a correction factor at a given wavelengths a function of {L}, {L*}, {r} and {D} and to apply the correction factor to R to determine R*.

26. The wavelength correction module of claim 25, wherein the set of light sources comprises a set of LEDs.

27. The wavelength correction module of claim 25, wherein the correction function module is configured to determine a correction factor $$c(R) = \left(\frac{\sum L_i * r_i D_i}{\sum L_i * D_i}\right) \Big/ \left(\frac{\sum L_i r_i D_i}{\sum L_i D_i}\right).$$

* * * * *